(12) United States Patent
Heismann et al.

(10) Patent No.: US 7,362,844 B2
(45) Date of Patent: Apr. 22, 2008

(54) TOMOGRAPHY APPLIANCE, AND METHOD FOR A TOMOGRAPHY APPLIANCE

(75) Inventors: Bjoern Heismann, Erlangen (DE); Silke Janssen, Giessen (DE)

(73) Assignee: Siemens Aktiengesellschaft, Munich (DE)

( * ) Notice: Subject to any disclaimer, the term of this patent is extended or adjusted under 35 U.S.C. 154(b) by 216 days.

(21) Appl. No.: 11/203,290

(22) Filed: Aug. 15, 2005

(65) Prior Publication Data

US 2006/0034418 A1    Feb. 16, 2006

(30) Foreign Application Priority Data

Aug. 16, 2004    (DE) ............... 10 2004 039 681

(51) Int. Cl.
*H05G 1/60* (2006.01)
(52) U.S. Cl. ............... 378/4; 378/210; 378/901
(58) Field of Classification Search ............. 378/4–21, 378/210, 901
See application file for complete search history.

(56) References Cited

U.S. PATENT DOCUMENTS

| | | | |
|---|---|---|---|
| 4,225,789 A | 9/1980 | Albrecht | 378/5 |
| 5,528,649 A | 6/1996 | Heidsieck | 378/56 |
| 5,633,499 A * | 5/1997 | Lim et al. | 250/363.07 |
| 5,777,338 A | 7/1998 | He | |
| 5,867,553 A | 2/1999 | Gordon et al. | 378/4 |
| 6,018,562 A * | 1/2000 | Willson | 378/9 |
| 6,754,298 B2* | 6/2004 | Fessler | 378/4 |
| 7,133,888 B2* | 11/2006 | Kohn et al. | 708/446 |
| 2003/0136913 A1 | 7/2003 | Haar | |
| 2004/0264626 A1* | 12/2004 | Besson | 378/4 |
| 2005/0063508 A1* | 3/2005 | Okamura | 378/19 |
| 2005/0084070 A1 | 4/2005 | Chretien | 378/111 |

FOREIGN PATENT DOCUMENTS

| | | |
|---|---|---|
| DE | 19502574 C2 | 8/1996 |
| DE | 10051162 A1 | 5/2002 |
| DE | 10 2004 001 185 A1 | 7/2004 |
| GB | 2 004 437 A | 2/1979 |
| WO | WO 97/16721 A1 | 5/1997 |

* cited by examiner

*Primary Examiner*—Courtney Thomas
*Assistant Examiner*—Alexander Taningco
(74) *Attorney, Agent, or Firm*—Harness, Dickey & Pierce

(57) ABSTRACT

A tomography appliance and method for a tomography appliance make it possible to calculate, in a simple and efficient manner, detector-element-related coefficients of an intensity function dependent on the detector output signal and to calculate the X-ray-emitter-related coefficients of an intensity function dependent on an X-ray emitter input value. This is done on the basis of measured detector output signals and at least one X-ray emitter input value, such that the intensity which acts precisely on the respective detector element can be determined from X-ray radiation originating from the X-ray emitter.

31 Claims, 3 Drawing Sheets

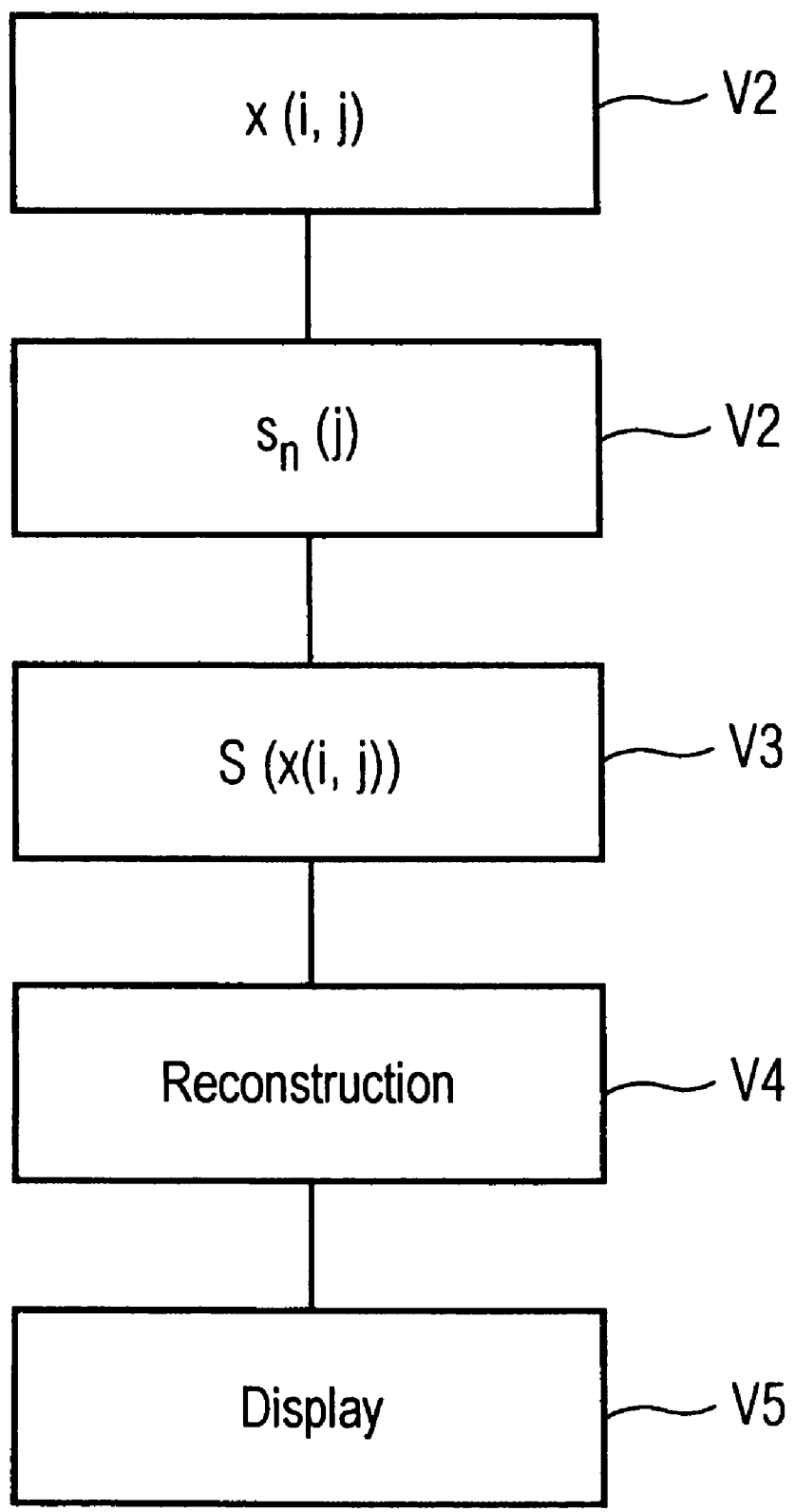

TOMOGRAPHY APPLIANCE, AND METHOD FOR A TOMOGRAPHY APPLIANCE

The present application hereby claims priority under 35 U.S.C. §119 on German patent application number DE 10 2004 039 681.7 filed Aug. 16, 2004, the entire contents of which is hereby incorporated herein by reference.

FIELD

The invention generally relates to a tomography appliance having an X-ray emitter and a detector, comprising a plurality of detector elements for production of detector output signals. The invention also generally relates to a method for a tomography appliance such as this.

BACKGROUND

A tomography appliance with an X-ray emitter and a detector is known, for example, from DE 195 02 574 C2. The detector includes a plurality of detector elements, which are arranged in a rectangular detector array formed from rows and columns. The X-ray emitter may in this case be an X-ray tube. However, any other desired sources of X-ray radiation are also feasible.

The detector elements are used for production of detector output signals as a measure of the absorption of X-ray radiation which originates from the X-ray emitter and passes through a measurement area. The detector and X-ray emitter are arranged such that they can be rotated about a rotation axis. It is thus possible to reconstruct a three-dimensional image, for example in order to examine the interior of the body of a patient, for an object positioned in the measurement area, on the basis of the detector output signals obtained from different rotation angle positions.

By way of example, scintillation detectors or semiconductor detectors may be used in a tomography appliance. The detector elements in a scintillation detector as known from DE 100 51 162 A1 each have a scintillator and a photodiode associated with it. In a detector such as this, the detector output signals are produced indirectly by means of light pulses, which are caused by absorption of X-ray quanta in the scintillator.

The detector elements of a semiconductor detector that is known from U.S. Pat. No. 5,77,338 in contrast to this each have a p-doped and n-doped semiconductor material with a depletion layer which is sensitive to X-ray radiation. The detector output signals from a semiconductor detector such as this are produced directly from the charge carriers caused by an X-ray quantum in the depletion layer.

Scintillation detectors are preferably operated as integrating detectors. In this operating mode, the detector output signal is integrated over a specific time. A good image quality can be achieved, particularly if the detector elements have a short decay time.

Semiconductor detectors are, in contrast to this, preferably operated as counting detectors. After the occurrence of an event, a counting detector requires a specific time, the so-called dead time, to process this event. All other events which occur during this time are lost. A distinction is drawn between two situations in the behavior of a detector in the counting operating mode:

(1) non-paralyzing:

After each verified event, the detector is not sensitive for a fixed time $\tau$, where $\tau$ corresponds to the dead time. It cannot register events which occur during this time (non-extendable dead time).

(2) paralyzing:

The detector remains sensitive even during the dead time. The dead time can thus be lengthened by the occurrence of a further event (extendable dead time).

When a large number of X-ray quanta arrive, there is a non-linear relationship between the measured counting rate and the counting rate which actually acts on a detector element.

The relationship between the measured and actual counting rate can be specified for detectors with a non-paralyzing behavior by $m=n/(1+n*\tau)$, and for detectors with a paralyzing behavior by $m=n*e^{-n\tau}$ where m is the measured counting rate, n is the actual counting rate, and $\tau$ is the dead time of the detector elements.

The measured counting rate can also be understood as the measured intensity of the X-ray radiation, and the additional counting rate can also be understood as the actual intensity of the X-ray radiation acting on a detector element. Thus, in order to simplify the description, the following text also uses the generally descriptive expression intensity rather than counting rate.

An error in the determined intensity of the X-ray radiation for the respective detector element at the time of an examination or at the time of a calibration of the tomography appliance leads to a deterioration in the achievable image quality in the reconstruction of a three-dimensional image on the basis of different projection images which have been recorded at different rotation angle positions.

SUMMARY

An object of at least one embodiment of the present invention is to specify tomography appliance and a method for a tomography appliance, which creates the preconditions for allowing the intensity of the X-ray radiation which actually acts on a detector element to be determined in a simple manner.

According to at least one embodiment of the invention, the tomography appliance has a computation device, which calculates detector-element-related coefficients of an intensity function (which is dependent on a detector output signal) and X-ray-emitter-related coefficients of an intensity function (which is dependent on an X-ray emitter input value) from detector output signals of at least one detector element, and from at least one predeterminable X-ray emitter input value of an X-ray emitter. The coefficients can be calculated by solving an equation system (which includes the coefficients, the detector output signals and the at least one X-ray emitter input value), which equations produce the relationship between the intensity function (which is dependent on a detector output signal) and the intensity function (which is dependent on an X-ray emitter input value).

The tomography appliance according to at least one embodiment of the invention allows simple calculation of the detector-element-related coefficients of the intensity function (which is dependent on the detector input signal) and of the X-ray-emitter-related coefficients of the intensity function which is dependent on the X-ray emitter input value, such that the intensity of the X-ray radiation acting on a detector element can be determined at any time, with little effort, following the calculation of the coefficients, which can be carried out before an examination. The coefficients are calculated just on the basis of detector output signals and selected X-ray emitter input values.

The intensity of the X-ray radiation at the location of a specific detector element in the case of the tomography appliance according to at least one embodiment of the invention is also possible, after calculation of the detector-element-related coefficients, at the time of an examination in conjunction with the intensity function which is dependent on the detector output signal. In the situation where no object is located in the measurement area, it is also possible to calculate the intensity acting on the detector elements by means of the X-ray-emitter-related coefficients in conjunction with the intensity function which is dependent on the X-ray emitter input value. The intensity of the actually acting X-ray radiation can thus be determined without any need for a complex measurement layout.

In one advantageous refinement of at least one embodiment of the invention, the detector-element-related coefficients can be used in conjunction with the intensity function (which is dependent on the detector output signal) for correction of a non-linear relationship between the intensity measured by the detector element and the intensity (which actually acts) of the X-ray radiation at the location of the detector element. A correction of the detector output signals such as this ensures that adjacent detector elements produce the same results even if they have different detector element characteristics, for example different dead times, for the same intensities of the X-ray radiation acting on them. The correction of the detector output signals thus improves the achievable image quality, particularly in the reconstruction of a three-dimensional image.

The non-linearity can also be corrected on the basis of the detector output signals in conjunction with the coefficients which can be determined from the intensity function in a highly cost-effective manner, furthermore, since there is no need for complex matching of the electronic components, in order to match the detector element characteristics, for signal correction.

Before the start of an examination, the intensity of the X-ray radiation, which is dependent on the object being examined, is generally set in the course of calibration of the tomography appliance, in order to achieve high image contrast. The X-ray-emitter-related coefficients can advantageously be used in conjunction with an intensity function which is dependent on the X-ray emitter input value for very precise adjustment of the intensity of the X-ray radiation acting on the detector elements, thus making it possible to improve the achievable image quality and the achievable image contrast of an X-ray.

An X-ray tube is preferably provided as the X-ray emitter, and a tube current is preferably provided as the X-ray emitter input value for the tomography appliance according to at least one embodiment of the invention, so that the intensity of the X-ray radiation produced by the X-ray tube can be predetermined by way of the selected tube current. The functional relationship between the tube current and the intensity of the X-ray radiation thus in this case results from the intensity function which is dependent on the tube current, in conjunction with the tube-current-related coefficients which can be calculated.

The intensity function, which is dependent on the X-ray emitter input value, may have a different form, depending on the accuracy requirements with respect to the determination of the intensity, or the computation time requirements with respect to the calculation of the coefficients.

In one advantageous refinement of the tomography appliance according to at least one embodiment of the invention, in which the coefficients of the intensity functions can be calculated in a particularly short computation time, the intensity function which is dependent on the X-ray emitter input value is a linear function of the following form:

$$Q1(y(i))=q0(i)+q1(i)*y(i) \tag{1}$$

where i is an index for a measurement, $q0(i), q1(i)$ are X-ray-emitter-related coefficients for a measurement i, and $y(i)$ is the X-ray emitter input value for the measurement i.

A further preferred form of the intensity function which is dependent on the X-ray emitter input value and in which the intensity of the X-ray radiation produced by the X-ray emitter is determined more accurately than by using a linear function is in the form of a square function:

$$Q2(y(i))=q0(i)+q1(i)*y(i)+q2(i)*y(i)^2 \tag{2}$$

where i is an index for a measurement, $q0(i), q1(i), q2(i)$ are X-ray-emitter-related coefficients for a measurement i, and $y(i)$ is the X-ray emitter input value for the measurement i.

One advantageous form of the intensity function which is dependent on the X-ray emitter input value and in which it is possible to ensure that the intensity of the X-ray radiation produced by the X-ray emitter is calculated with very little error, although this requires more computation time in order to determine the coefficients, is in the form of a cubic function:

$$Q3(y(i))=q0(i)+q1(i)*y(i)+q2(i)*y(i)^3 \tag{3}$$

where i is an index for a measurement, $q0(i), q1(i), q2(i), q3(i)$ are X-ray-emitter-related coefficients for a measurement i, and $y(i)$ is the X-ray emitter input value for the measurement i.

The relationship between the intensity function (which is dependent on a detector output signal) and the intensity function (which is dependent on an X-ray emitter input value) at the position of the detector element is advantageously given by the following equation:

$Q(y(i))=S(x(i,j))$, where $Q(y(i))$ represents, in a general form, the intensity function which is dependent on the X-ray emitter input value $y(i)$, and $S(x(i,j))$ represents, in a general form, the intensity function which is dependent on the detector output signal $x(i,j)$.

The detectors in the tomography appliance according to at least one embodiment of the invention can be operated in different operating modes.

The detector, for example a semiconductor detector, can advantageously be operated as a counting detector. The intensity function which is dependent on the detector output signal has the following preferred form for counting detectors with a non-paralyzing behavior:

$$S1(x(i,j))=x(i,j)/(1-x(i,j)*\tau(j)) \text{ where} \tag{4}$$

i is an index for a measurement, j is an index for the detector element, $x(i,j)$ is the detector output signal from the j-th detector element for the measurement i, and $\tau(j)$ is the dead time of the j-th detector element.

The dead time $\tau(j)$ in this case corresponds to the processing time which a detector element requires in order to process an arriving X-ray quantum. The detector element cannot register any other X-ray quantum during this processing time. The processing time may differ widely from one detector element to another, and should thus be known individually for each detector element, as a function of the detector. The dead time $\tau(j)$ corresponds to the detectorelement-related coefficients with which the detector element characteristics and the non-linear relationship between the detector output signal and the intensity of the X-ray radiation acting on the detector element can be characterized.

In one advantageous refinement of at least one embodiment of the invention, the equation system which can be solved in order to calculate the coefficients of the intensity functions can be formed for counting detectors from the following equations:

$$Q1(y(i))=S1(x(i,j)) \quad (5)$$

which also corresponds to the following form:

$$q0(i)+q1(i)*y(i)=x(i,j)/(1-x(i,j)*\tau(j)).$$

However, it is also possible to use detectors, for example scintillation detectors, in an integrating operating mode for the tomography appliance according to at least one embodiment of the invention. The intensity function (which is dependent on the detector output signal) can in this case preferably be represented as a square function of the following form:

$$S2(x(i,j))=s0(j)+s1(j)*x(i,j)+s2(j)*x(i,j)^2 \quad (6)$$

where i is an index for a measurement, j is an index for the detector element, $x(i,j)$ is the detector output signal from the j-th detector element for the measurement i, and $s0(j), s1(j), s2(j)$ are detector-element-related coefficients for the j-th detector element.

The intensity function which is dependent on the detector output signal and is in the form of a square function allows the detector element characteristics to be described with only a small error, and at the same time ensures quick and simple solution of the equation system formed by this function, in order to determine the coefficients.

The equation system can preferably be solved on the basis of a non-linear optimization method in order to determine the detector-element-related and X-ray-emitter-related coefficients. Non-linear optimization methods, such as the Simplex method or the Levenberg-Marquard method, make it possible in particular to efficiently determine the sought detector-element-related and X-ray-emitter-related coefficients with little effort.

In one advantageous refinement of at least one embodiment of the invention, the tomography appliance has a memory which can be used to store the detector-element-related and X-ray-emitter-related coefficients which can be calculated. Thus, it is possible to create direct access to the coefficients at any time, even after the calculation.

According to at least one embodiment of the invention, the method for a tomography appliance includes the following method steps:

determination of the detector output signals for at least one detector element for at least one predeterminable X-ray emitter input value of the X-ray emitter, and calculation of detector-element-related coefficients of an intensity function (which is dependent on the detector output signal) and of X-ray-emitter-related coefficients of an intensity function (which is dependent on an X-ray emitter input value) on the basis of the determined detector output signals and of the at least one X-ray emitter input value, with the coefficients being calculated by solving an equation system which comprises the coefficients, the detector output signals and the at least one X-ray emitter input value, which equations produce the relationship between the intensity function (which is dependent on a detector output signal) and the intensity function (which is dependent on an X-ray emitter input value).

BRIEF DESCRIPTION OF THE DRAWINGS

Example embodiments of the invention as well as further advantageous refinements of the invention as claimed in the dependent claims are illustrated in the following schematic drawings, in which:

FIG. 3 shows a method according to at least one embodiment of the invention for correction of detector output signals and for reconstruction of a three-dimensional image in the form of a block diagram.

DETAILED DESCRIPTION OF THE EXAMPLE EMBODIMENTS

Figure 1:
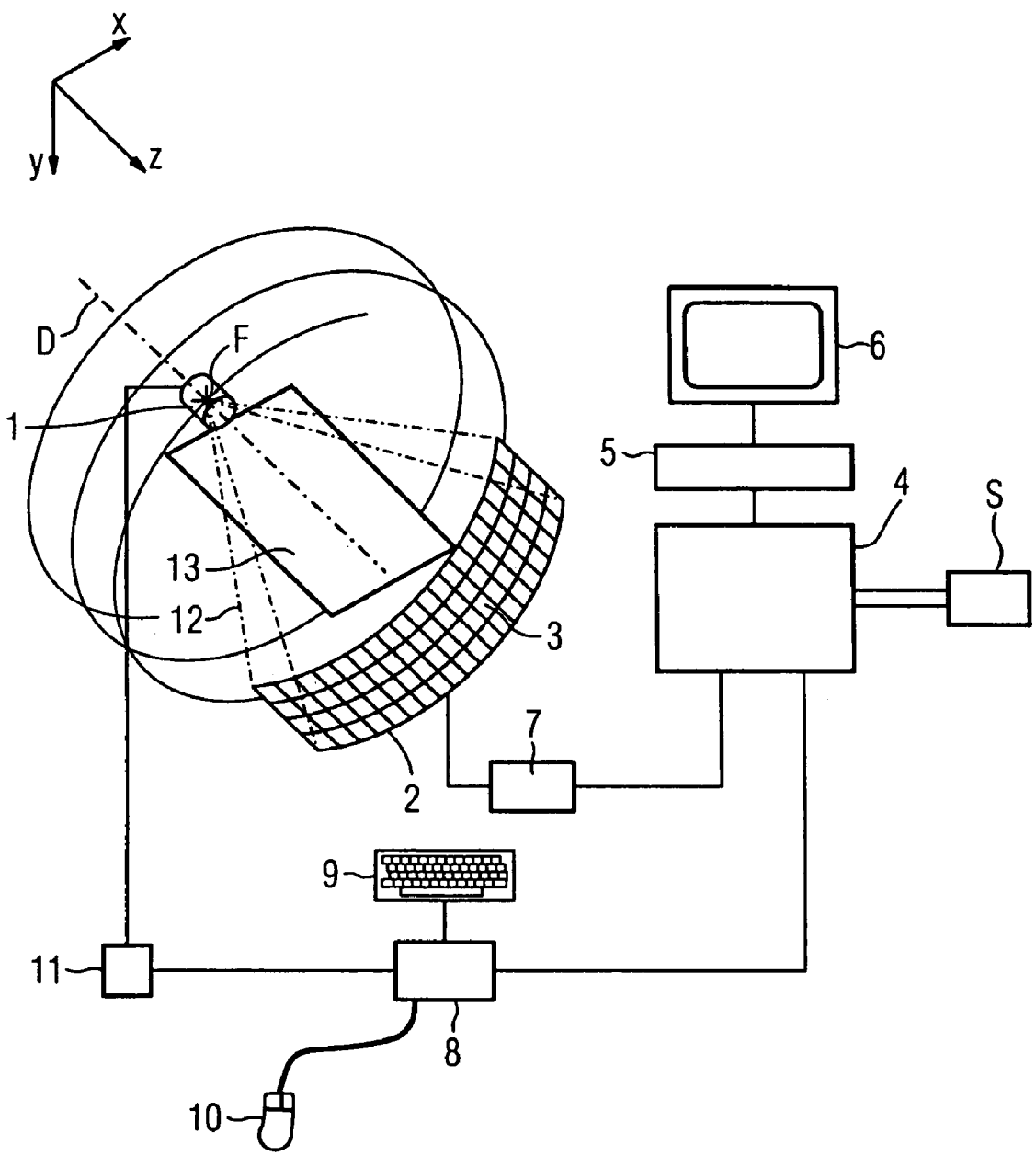
FIG. 1 shows an illustration, partially in perspective form and partially in the form of a block diagram, of a tomography appliance according to at least one embodiment of the invention with a detector and an X-ray emitter.

FIG. 1 shows a tomography appliance according to an embodiment of the invention, in this case in the form of an X-ray computer tomography appliance, illustrated partially in perspective form and partially in the form of a block diagram. The tomography appliance includes an X-ray emitter in the form of an X-ray tube 1, a detector 2 which has detector elements 3 arranged to form rows and columns in a detector array, computation device 4 for calculation of the detector-element-related and X-ray-tube-related coefficients, and for determination of the intensity of the X-ray radiation, a reconstruction unit 5 and a display unit 6. The X-ray radiation produced by the X-ray emitter in the form of an X-ray tube is adjusted by way of a predeterminable X-ray emitter input value in the form of a tube current.

The X-ray tube 1 and the detector 2 are part of a recording system and are fitted opposite one another on a rotating frame, which is not illustrated, such that an X-ray beam which originates from a focus F of the X-ray tube 1 and is bounded by edge beams 12 strikes the detector 2 during operation of the tomography appliance.

The rotating frame can be caused to rotate about a rotation axis D by way of a drive device, which is not illustrated. The rotation axis D in this case runs parallel to the z-axis of a three-dimensional, right-angled coordinate system illustrated in FIG. 1. This allows X-rays to be produced from different projection directions and rotation angle positions of the recording system for an object which is not illustrated but is located on a measurement table 13, in order to reconstruct a three-dimensional image.

The X-ray tube 1 uses the tube current, as set by a control unit 8 and produced by a generator 11, to produce X-ray radiation of specific intensity, which passes through an object positioned in the measurement area and then strikes the detector elements 3 of the detector 2. The tube current which is set by the control unit 8 can be preset by an operator by means of a keyboard 9 or a mouse 10.

The detector output signals which are produced by the detector elements 3 and are read by a read unit 7 in this case represent the intensities of the X-ray radiation absorbed in the measurement area, with the measured intensities differing from one another by the intensities which actually strike the detector element 3. There is a non-linear relationship between the measured and effective intensities, and this relationship depends on the functional principle and on the electronic components of the detector 2 used for signal processing.

The detector 2 used in this example embodiment is a semiconductor detector, and has a depletion layer, which is sensitive to X-ray radiation, between an n-doped and a p-doped semiconductor material. In this exemplary embodiment, the detector is operated in a counting operating mode.

The computation device(s) may be, in each case, connected via a link to the read unit 7 and to the control unit 8. This allows the detector output signals that are read and the associated selected tube current for each measurement to be transmitted to the computation device(s) 4.

A plurality of measurements are generally carried out, in each case with different tube currents, without any object in the measurement area in order to determine the detector-element-related coefficients and the X-ray-tube-related coefficients. The detector output signals read for each measurement are transmitted together with the associated tube current to the computation device(s) 4. In this case, the detector output signals and the tube current in each case form a measurement series.

By way of example, a total of M=3 measurements can be carried out with the tube currents of y(i)=50 mA, 100 mA and 150 mA, for each of which detector output signals from, for example, N=3×3=9 adjacent detector elements 3 in the detector 2 are read, and are transmitted together with the associated tube current to the computation device(s) 4. In the case of the example embodiment quoted, the tube voltage remains constant for each of the measurements, and is, for example, 80 kV.

The N adjacent detector elements 3 are intended to be subjected to essentially the same X-ray radiation intensity. This condition is satisfied in an adequate form by the spatial angle covered by a detector element 3 being small in comparison to the distance between the focus F and the detector element 3. In the case of X-ray radiation that is introduced via a form filter, the detector elements 3 located along the z-axis can preferably be used in order to calculate the coefficients.

The computation device(s) 4 use the measured values from the M measurements determined in this way to calculate the detector-element-related coefficients of an intensity function which is dependent on the detector output signal and the X-ray-tube-related coefficients of an intensity function which is dependent on the tube current.

The detector-element-related coefficients can be used in conjunction with the intensity function which is dependent on the detector output signal in order to correct the non-linearity between the intensities or detector output signals as measured by the detector elements, and the actual intensity of the X-ray radiation. Differences in the transfer functions (which indicate the relationship between the effective intensity and the resultant detector output signal) between the detector elements can thus be compensated for by, for example, all of the detector elements 3 producing the same results when the X-ray radiation has a homogenous intensity distribution.

A memory S, which is connected to the computation device(s), ensures storage of the calculated detector-element-related and X-ray-tube-related coefficients, thus allowing direct access to the coefficients at any time, even after the calculation, for example during the examination of an object introduced into the measurement area.

A reconstruction unit 5, which is connected to the computation device(s) 4, allows the calculation of a three-dimensional image on the basis of corrected detector output signals during an examination in which project recordings of an object are made from different projection directions, thus improving the achievable image quality.

A display unit 6, which is connected to the reconstruction unit 5, is used to display the three-dimensional image.

Figure 2:
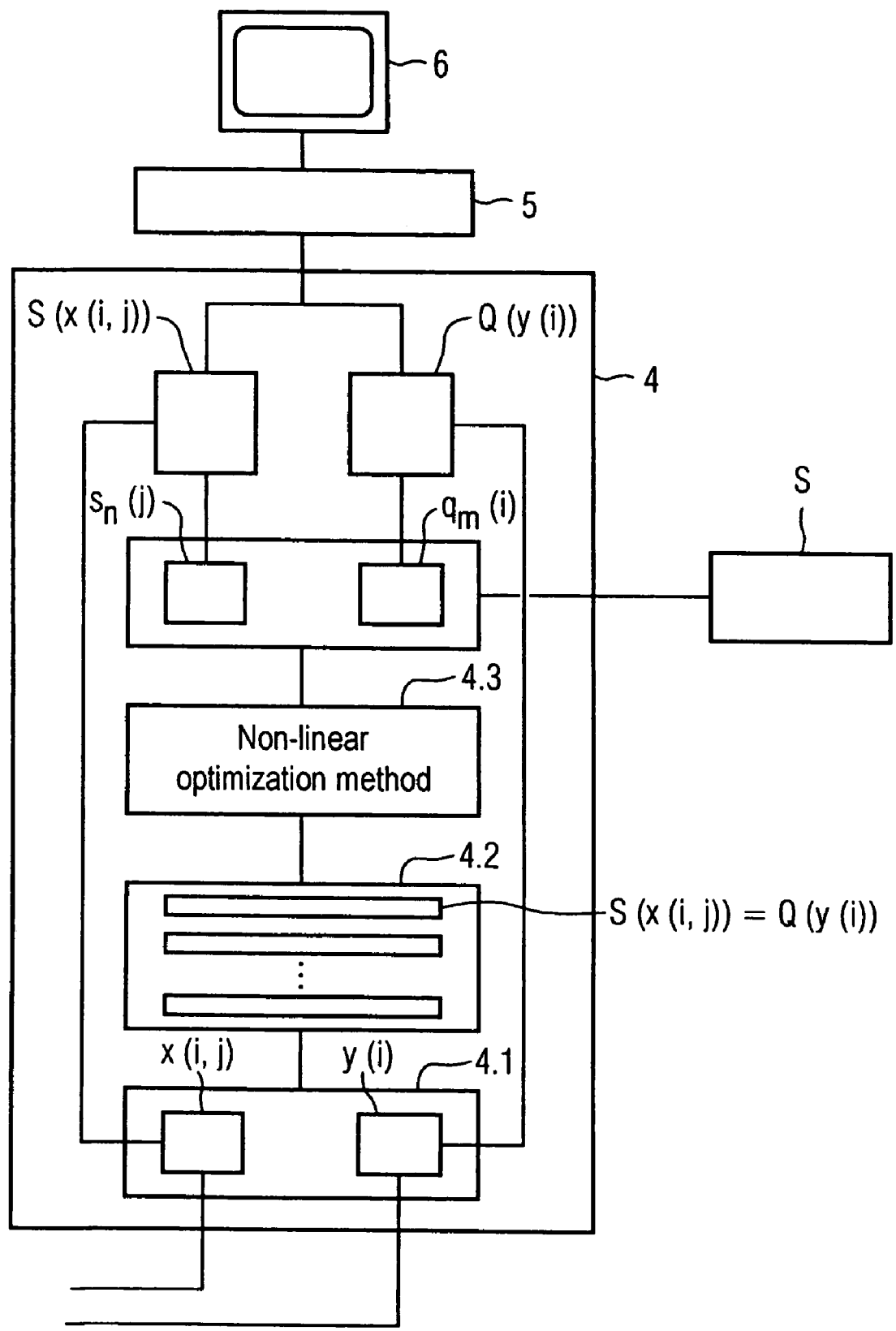
FIG. 2 shows a detailed view of the computation device from FIG. 1.

FIG. 2 shows a detailed view of the computation device(s) 4 illustrated in FIG. 1. The detector-element-related coefficients $s_n(j)$ of an intensity function $S(x(i,j))$ which is dependent on the detector output signal, and the X-ray-tube-related coefficients $q_m(i)$ of an intensity function $Q(y(i))$ which is dependent on the tube current are calculated, as already explained with reference to FIG. 1, on the basis of M measurements, with one measurement series being formed for each measurement from N detector output signals $x(i,j)$ and from the associated tube current $y(i)$.

The X-ray radiation intensity which actually acts on a detector element 3 can be determined both by way of an intensity function $S(x(i,j))$ which is dependent on the detector output signal and has n unknown detector-element-related coefficients $s_n(j)$, and by way of an intensity function $Q(y(i))$, which is dependent on the tube current and has m unknown X-ray-tube-related coefficients $q_m(i)$. Together, the functions form an intensity equation with a total of n+m unknown coefficients:

$$S(x(i,j))=Q(y(i))$$

The intensity function $S(x(i,j))$, which is dependent on the detector output signal, of the semiconductor detector used in the exemplary embodiment is given, by way of example, by the following equation for a paralyzing detector behavior:

$$S1(x(i,j))=x(i,j)/(1-x(i,j)*\tau(j)),$$

where i is an index for a measurement, j is an index for the detector element, $x(i,j)$ is the detector output signal from the j-th detector element for the measurement i, and $\tau(j)$ is one detector-element-related coefficient $s_n(j)$ of the j-th detector element.

The intensity function $Q(y(i))$, which is dependent on the tube current, can be stated, for example, in a particularly simple manner by a linear function of the following form:

$$Q1(y(i))=q0(i)+q1(i)*y(i),$$

where i is the index for a measurement, $q0(i), q1(i)$ are the two X-ray-tube-related coefficients $q_m(i)$ for a measurement i, and $y(i)$ is the tube current for the measurement i.

The relationship for the intensity equation is thus as follows:

$$S1(x(i,j))=Q1(y(i)) \text{ and}$$

$$x(i,j)/(1-x(i,j)*\tau(j))=q0(i)+q1(i)*y(i).$$

The intensity functions quoted here have only an exemplary character and, depending on the detector 2 or the X-ray emitter 1, may have a different form or a different number of detector-element-related coefficients $s_n(j)$ and X-ray-tube-related coefficients $q_m(i)$.

The measurement series determined from the measurements are substituted into the intensity equation. The equation system thus indicated by 4.2 in FIG. 3 has a total of M*m+N*n unknowns, where M is the number of measurements carried out in order to calculate the coefficients, N is the number of detector elements read, m is the number of X-ray-tube-related coefficients $q_m(i)$ and n is the number of detector-element-related coefficients $s_n(j)$.

The following relationship must be satisfied in order to allow the equation system to be solved:

$M*N \geq M*m+N*n.$

As is immediately evident from this relationship, at least two detector elements must be read in order to solve the equation system.

The unknown detector-element-related coefficients $s_n(j)$ and the unknown X-ray-tube-related coefficients $q_m(i)$ are calculated by solving the equation system 4.2 on the basis of a non-linear optimization method 4.3. By way of example, an equation system 4.2 such as this can be solved in an efficient and simple manner using a Levenberg-Marquard method or a Simplex method, as known from Kosmol: Optimierung und Approximation [Optimization and Approximation], De Gruyter 1991.

The detector-element-related coefficients $s_n(j)$ which can be determined in this way and the X-ray-tube-related coefficients $q_m(i)$ which can be determined in this way can be stored in a memory S and are available, even after the calculation, for correction of the detector output signals $x(i,j)$ or for calculation of the intensity on the basis of the tube current $y(i)$.

The coefficients $s_n(j), q_m(i)$, which are calculated or are read from the memory S, can be used in conjunction with the respective intensity function $S(x(i,j))$ or $Q(y(i))$ in order to determine the X-ray radiation intensity acting on a respective detector element 3. The detector-element-related coefficients $s_n(j)$ can be used together with the intensity function $S(x(i,j))$ which is dependent on the detector output signal for correction of incoming detector output signals $x(i,j)$, in such a way that the corrected detector output signal corresponds to the intensity actually acting on the detector element 3. The X-ray-tube-related coefficients $q_m(i)$ can be used together with the intensity function $Q(y(i))$ which is dependent on the tube current in order to set an X-ray radiation intensity acting on the detector elements 3, without any object positioned in the measurement area.

The detector-element-related coefficients $s_n(j)$ are associated with those detector elements which have been read during the measurements. In order to save computation time, the known detector-element-related coefficients $s_n(j)$ can be used, on the assumption that all of the detector elements 3 have similar detector element characteristics, so that the detector-element-related coefficients which are required for correction are also calculated, for example by averaging, for those detector elements which are not taken into account in the measurement. This makes it possible to correct the detector output signals $x(i,j)$ from all of the detector elements 3 associated with the detector 2, even though only a relatively small number N of the detector elements are taken into account in the measurements.

The corrected detector output signals are transmitted to the reconstruction unit 5, where they are processed to form a three-dimensional image. The result image is displayed via the display unit 6 that is connected to the reconstruction unit 5.

FIG. 3 shows a method of one embodiment for calculation of the X-ray radiation intensity which actually acts on a detector element, for correction of detector output signals $x(i,j)$, and for reconstruction of a three-dimensional image in the form of a block diagram. In a first method step V1, the detector output signals $x(i,j)$ and a tube current $y(i)$ associated with that recording are transmitted to the computation device(s) 4 via the read unit 7, which is shown in FIG. 1, and the control unit 8. In a second method step V2, the detector-element-related coefficients $s_n(j)$, which have already been calculated in advance, are read from the memory S. The X-ray radiation intensity acting on the respective detector element 3 is in each case calculated in a subsequent third method step V3 from the detector-element-related coefficients $s_n(j)$ and from the detector output signal $x(i,j)$ by use of an intensity function $S(x(i,j))$ which is dependent on the detector output signal. The detector output signals that have been corrected in this way are transmitted in a fourth method step V5 to the reconstruction unit 5, and are used to calculate a three-dimensional image, which is displayed on a display unit 6, in a fifth method step V5.

An idea of at least one embodiment of the invention can be summarized as follows: the tomography appliance according to at least one embodiment of the invention and/or the method according to at least one embodiment of the invention for a tomography appliance allow the calculation in a simple and efficient manner of detector-element-related coefficients $s_n(j)$ of an intensity function $S(x(i,j))$ which is dependent on a detector output signal, and the calculation of X-ray-emitter-related coefficients $q_m(i)$ of an intensity function $Q(y(i))$, which is dependent on an X-ray emitter input value, on the basis of measured detector output signals $x(i,j)$ and of at least one X-ray emitter input value $y(i)$, so that it is possible to determine an accurate intensity, acting on the respective detector element (3), of X-ray radiation originating from the X-ray emitter (1).

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A tomography appliance, comprising:
    an X-ray emitter; and
    a detector, including a plurality of detector elements for production of detector output signals; and
    at least one computation device to calculate detector-element-related coefficients of an intensity function dependent on a detector output signal and X-ray-emitter-related coefficients of an intensity function dependent on an X-ray emitter input value from the detector output signals of at least one detector element and from at least one predeterminable X-ray emitter input value of the X-ray emitter, wherein the coefficients are calculatable by solving an equation system including the coefficients, the detector output signals and the at least one X-ray emitter input value, which equations produce the relationship between the intensity function dependent on a detector output signal and the intensity function dependent on an X-ray emitter input value.

2. The tomography appliance as claimed in claim 1, wherein the calculatable detector-element-related coefficients are usable in conjunction with the intensity function dependent on a detector output signal for correction of a non-linear relationship between the detector output signals and an intensity of the X-ray radiation emitted from the X-ray emitter.

3. The tomography appliance as claimed in claim 1, wherein the calculatable X-ray-emitter-related coefficients are usable in conjunction with the intensity function dependent on an X-ray emitter input value for adjustment of an intensity of the X-ray radiation which is emitted from the X-ray emitter and acts on a detector element.

4. The tomography appliance as claimed in claim 1, wherein the X-ray emitter is an X-ray tube, and the X-ray emitter input value is a tube current.

5. The tomography appliance as claimed in claim 1, wherein the intensity function Q(y(i)) which is dependent on the X-ray emitter input value is a linear function of the following form:

$$Q1(y(i))=q0(i)+q1(i)*y(i) \text{ where}$$

i is an index for a measurement, q0(i),q1(i) are X-ray-emitter-related coefficients for a measurement i, and y(i) is the X-ray emitter input value for the measurement i.

6. The tomography appliance as claimed in claim 1, wherein the intensity function Q(y(i)) which is dependent on the X-ray emitter input value is a square function of the following form:

$$Q2(y(i))=q0(i)+q1(i)*y(i)+q2(i)*y(i)^2 \text{ where}$$

i is an index for a measurement, q0(i),q1(i),q2(i) are X-ray-emitter-related coefficients for a measurement i, and y(i) is the X-ray emitter input value for the measurement i.

7. The tomography appliance as claimed in claim 1, wherein the intensity function Q(y(i)) which is dependent on the X-ray emitter input value is a cubic function of the following form:

$$Q3(y(i))=q0(i)+q1(i)*y(i)+q2(i)*y(i)^2+q3(i)*y(i)^3 \text{ where}$$

i is an index for a measurement, q0(i),q1(i),q2(i),q3(i) are X-ray-emitter-related coefficients for a measurement i, and y(i) is the X-ray emitter input value for the measurement i.

8. The tomography appliance as claimed in claim 1, wherein the relationship between the intensity function S(x(i,j)) dependent on a detector output signal and the intensity function Q(y(i)) dependent on an X-ray emitter input value is given by the following equation:

$$Q(y(i))=S(x(i,j)).$$

9. The tomography appliance as claimed in claim 1, wherein the detector is operatable as a counting detector.

10. The tomography appliance as claimed in claim 9, wherein the intensity function S(x(i,j)) dependent on a detector output signal for a paralyzing behavior on the detector is given by a function $$S1(x(i,j))=x(i,j)/(1-x(i,j)*\tau(j)) \text{ where}$$

i is an index for a measurement, j is an index for the detector element, x(i,j) is the detector output signal from the j-th detector element for the measurement i, and τ(j) is the dead time of the j-th detector element.

11. The tomography appliance as claimed in claim 10, wherein the relationship between the intensity function S(x(i,j)) dependent on a detector output signal and the intensity function Q(y(i)) dependent on an X-ray emitter input value is given by the following equation:

$$Q1(y(i))=S1(x(i,j)).$$

12. The tomography appliance as claimed in claim 1, wherein the detector is operatable as a integrating detector.

13. The tomography appliance as claimed in claim 12, wherein the intensity function S(x(i,j)) dependent on the detector output signal is represented by a square function of the following form:

$$S2(x(i,j))=s0(j)+s1(j)*x(i,j)+s2(j)*x(i,j)^2 \text{ where}$$

i is an index for a measurement, j is an index for the detector element, x(i,j) is the detector output signal from the j-th detector element for the measurement i, and s0(j),s1(j),s2(j) are detector-element-related coefficients for the j-th detector element.

14. The tomography appliance as claimed in claim 1, wherein the equation system is solvable on the basis of a non-linear optimization method.

15. The tomography appliance as claimed in claim 1, wherein a memory is provided for storage of the coefficients.

16. A method for a tomography appliance having an X-ray emitter and a detector including a plurality of detector elements for production of detector output signals, the method comprising:

determining the detector output signals for at least one detector element for at least one predeterminable X-ray emitter input value of the X-ray emitter;

calculating detector-element-related coefficients of an intensity function dependent on the detector output signal and X-ray-emitter-related coefficients of an intensity function dependent on an X-ray emitter input value on the basis of the determined detector output signals and of the at least one X-ray emitter input value, with the coefficients being calculated by solving an equation system which includes the coefficients, the detector output signals and the at least one X-ray emitter input value, which equations produce the relationship between the intensity function dependent on a detector output signal and the intensity function dependent on an X-ray emitter input value;

correcting the detector output signals based on at least one of the calculated detector-element-related coefficients and the X-ray-emitter-related coefficients;

reconstructing an image based on the corrected detector output signals; and displaying the reconstructed image.

17. The method as claimed in claim 16, wherein the calculatable detector-element-related coefficients are used in conjunction with the intensity function dependent on the detector output signal for correction of a non-linear relationship between the detector output signals and the intensity acting on the detector elements of the X-ray radiation emitted from the X-ray emitter.

18. The method as claimed in claim 16, wherein the calculated X-ray-emitter-related coefficients are used in conjunction with the intensity function dependent on an X-ray emitter input value for adjustment of an intensity of the X-ray radiation which is emitted from the X-ray emitter and acts on the detector element.

19. The method as claimed in claim 16, wherein the X-ray emitter is an X-ray tube, and the X-ray emitter input value is a tube current.

20. The method as claimed in claim 16, wherein the intensity function Q(y(i)) which is dependent on the X-ray emitter input value is a linear function of the following form:

$$Q1(y(i))=q0(i)+q1(i)*y(i) \text{ where}$$

i is an index for a measurement, q0(i),q1(i) are X-ray-emitter-related coefficients for a measurement i, and y(i) is the X-ray emitter input value for the measurement i.

21. The method as claimed in claim 16, wherein the intensity function Q(y(i)) which is dependent on the X-ray emitter input value is a square function of the following form:

$$Q2(y(i))=q0(i)+q1(i)*y(i)+q2(i)*y(i)^2 \text{ where}$$

i is an index for a measurement, q0(i),q1(i),q2(i) are X-ray-emitter-related coefficients for a measurement i, and y(i) is the X-ray emitter input value for the measurement i.

22. The method as claimed in claim 16, wherein the intensity function Q(y(i)) which is dependent on the X-ray emitter input value is a cubic function of the following form:

$$Q3(y(i))=q0(i)+q1(i)*y(i)+q2(i)*y(i)^2+q3(i)*y(i)^3$$
where i is an index for a measurement, q0(i),q1(i),q2(i),q3(i) are X-ray-emitter-related coefficients for a measurement i, and y(i) is the X-ray emitter input value for the measurement i.

23. The method as claimed in claim 16, wherein the relationship between the intensity function S(x(i,j)) dependent on a detector output signal and the intensity function Q(y(i)) dependent on an X-ray emitter input value is given by the following equation:

$$Q(y(i))=S(x(i,j)).$$

24. The method as claimed in claim 16, wherein the detector is operated as a counting detector.

25. The method as claimed in claim 24, wherein the intensity function S(x(i,j)) dependent on a detector output signal for a paralyzing behavior on the detector is given by a function $$S1(x(i,j))=x(i,j)/(1-x(i,j)*\tau(j)) \text{ where}$$

i is an index for a measurement, j is an index for the detector element, x(i,j) is the detector output signal from the j-th detector element for the measurement i, and τ(j) is the dead time of the j-th detector element.

26. The method as claimed in claim 25, wherein the relationship between the intensity function S(x(i,j)) dependent on a detector output signal and the intensity function Q(y(i)) dependent on an X-ray emitter input value is given by the following equation:

$$Q1(y(i))=S1(x(i,j)).$$

27. The method as claimed in claim 16, wherein the detector is operatable as a integrating detector.

28. The method as claimed in claim 27, wherein the intensity function S(x(i,j)) dependent on the detector output signal can be represented by means of a square function of the following form:

$$S2(x(i,j))=s0(j)+s1(j)*x(i,j)+s2(j)*x(i,j)^2 \text{ where}$$

i is an index for a measurement, j is an index for the detector element, x(i,j) is the detector output signal from the j-th detector element for the measurement i, and s0(j),s1(j),s2(j) are detector-element-related coefficients for the j-th detector element.

29. The method as claimed in claim 16, wherein the equation system is solvable on the basis of a non-linear optimization method.

30. The method as claimed in claim 16, wherein a memory is provided for storage of the coefficients.

31. An apparatus for a tomography appliance having an X-ray emitter and a detector including a plurality of detector elements for production of detector output signals, the apparatus comprising:

means for determining the detector output signals for at least one detector element for at least one predeterminable X-ray emitter input value of the X-ray emitter; and means for calculating detector-element-related coefficients of an intensity function dependent on the detector output signal and of X-ray-emitter-related coefficients of an intensity function dependent on an X-ray emitter input value on the basis of the determined detector output signals and of the at least one X-ray emitter input value, with the coefficients being calculated by solving an equation system which includes the coefficients, the detector output signals and the at least one X-ray emitter input value, which equations produce the relationship between the intensity function dependent on a detector output signal and the intensity function dependent on an X-ray emitter input value.

* * * * *